United States Patent [19]

Rambosek et al.

[11] 4,143,658
[45] Mar. 13, 1979

[54] INTRATRACHEAL INJECTION SYSTEM FOR ANIMALS

[75] Inventors: G. Phillip Rambosek, Maplewood; Charles G. Thiel, St. Paul, both of Minn.

[73] Assignee: Minnesota Mining and Manufacturing Company, St. Paul, Minn.

[21] Appl. No.: 771,476

[22] Filed: Feb. 24, 1977

Related U.S. Application Data

[60] Continuation of Ser. No. 597,545, Jul. 21, 1975, abandoned, which is a division of Ser. No. 505,668, Sep. 13, 1974, Pat. No. 3,915,165.

[51] Int. Cl.² .................................................. A61M 5/32
[52] U.S. Cl. .............................. 128/184; 128/218 N; 128/221; 128/215; 128/351
[58] Field of Search ............ 128/351 R, 349 R, 350 R, 128/348, DIG. 26, DIG. 9, 218 N, 221, 347, 214.4, 184, 223, 145.8, 215

[56] References Cited

U.S. PATENT DOCUMENTS

| 1,527,291 | 2/1925 | Zorraquin | 128/347 |
| 2,630,803 | 3/1953 | Baran | 128/221 |
| 3,081,770 | 3/1963 | Hunter | 128/221 |
| 3,630,198 | 12/1971 | Henkin | 128/215 |

Primary Examiner—Henry J. Recla
Attorney, Agent, or Firm—Cruzan Alexander; Donald M. Sell; Carolyn A. Bates

[57] ABSTRACT

A system is disclosed for injecting dry medicaments in a gaseous suspension into the trachea of an animal. The system comprises: needle means for insertion into the trachea and having a passageway for directing the medicament into the trachea; medicament dispenser for dispensing the medicament into the needle means; a mask formed from substantially gas inpermeable material and shaped to fit over the mouth and nose of the animal having an opening for the movement of gas thereto; and regulator means adapted for connection to a supply of compressed gas connected to the mask and the needle means to time the discharge of compressed gas to the mask and the needle means to coincide with the animal's inhalation.

1 Claim, 8 Drawing Figures

INTRATRACHEAL INJECTION SYSTEM FOR ANIMALS

This is a continuation of application Ser. No. 597,545 filed July 21, 1975, now abandoned, which is a division of application Ser. No. 505,668, filed Sept. 13, 1974, now U.S. Pat. No. 3,915,165.

FIELD OF THE INVENTION

This invention relates to a system for treating respiratory diseases in animals. More specifically, this invention relates to a system for injecting medicaments into the trachea of an animal with compressed gas under the control of an automatic positive pressure breathing apparatus.

DISCUSSION OF THE PRIOR ART

Pneumonia ranks as one of the most serious health problems in livestock. It has been estimated that this disease results in a pecuniary loss to cattle producers in this country of about one hundred million dollars each year. (Livestock Conservation, Inc., National Shipping Fever Survey, 1973). When considering the decreased weight gain of animals suffering from chronic pneumonia, the cost of medication and man hours required for treating the disease, the actual dollar loss is probably much larger.

The term "pneumonia" refers broadly to an inflammation of the lungs. The cause of the disease is usually attributed to a microorganism of some type, but various physical and chemical irritants can also contribute to the inflammation. Regardless of its etiology, the response of the lungs to the disease is well established. A fluid exudate is produced which results in congestion. The fluid exudate is gradually replaced by fibrin and the affected lung tissue solidifies into a firm, solid mass.

If the disease is controlled, the products of inflammation are broken down and removed by the body's normal repair mechanism in a process called "resolution." If resolution is delayed, irreversible changes may occur, resulting in permanent loss of pulmonary function.

Pneumonia is generally treated with antibiotics to eliminate infectious organisms. In addition, certain medicaments, particularly proteolytic enzymes such as streptokinase and streptodornase, can be administered to the animal to aid in the resolution process by breaking down fibrin and other products of inflammation.

In order to maximize the effectiveness of proteolytic enzymes, they should be delivered directly to the affected areas of the lungs by inhalation means. However, prior to the present invention, there were no practical means available for accomplishing this mode of drug delivery in animals.

Inhalation therapy in the treatment of respiratory diseases in humans has been practiced successfully for many years. Techniques and devices for delivering oxygen and medicaments to the lungs of human patients have become increasingly sophisticated in recent years. Automatic breathing units have been developed which respond to the patients normal respiration and afford the discharging of air or air-oxygen mixtures and medicament aerosols during the inhalation phase of respiration, thereby insuring that the medicament is delivered to an expanded lung.

Respirator systems for human therapy normally utilize a mask or mouthpiece device for directing the air or oxygen and medicament into the nose and/or mouth of the patient. Directing the medicament aerosols into the nose or oral cavity of a human is somewhat inefficient since a certain amount of the medicament is inevitably swallowed by the patient or becomes deposited on the mucosa of the nose, mouth and throat. This problem becomes greatly magnified when treating animals, especially livestock animals such as cows and pigs. Obviously, animals cannot be taught to cooperate with the breathing device in the same manner as humans. More importantly, the anatomical differences between the oral cavities of humans and animals are significant. Livestock such as cattle, horses and swine, because of their elongated snouts, have a larger surface area in the interior of the nose, mouth and upper throat region upon which an aerosol medicament may become deposited. In addition, the nasal passages of these animals have efficient filtering hairs to trap particulate matter. It is, therefore, extremely difficult to insure that even a minimum amount of a predetermined dosage of suspended medicament will reach the animal's lungs when discharged into the nose and/or mouth.

Because effective means for delivering medicaments to animals in a gaseous suspension have been heretofore unavailable, veterinarians have resorted, in certain cases, to intratracheal injection of liquid medicaments with a syringe and hypodermic needle. This method of treatment has several serious disadvantages. When the medicament is administered as a solution it drains by gravity means into the lower regions of the lung and does not become uniformly distributed throughout the lung tissue. Additional disadvantages are inherent in a method which introduces a liquid into an inflamed area which is already suffering from the presence of excess fluid. In such a case, a liquid medicament may initially aggrevate rather than alleviate the disease.

It is apparent from the above discussion that a need existed for a practical means of delivering dry medicaments in gaseous suspensions to the lungs of animals.

The present invention provides a system which will deliver a measured dosage of a dry medicament in a gaseous suspension to the lungs of an animal.

It is also intended that this invention will provide a system which will direct a gas-suspended medicament into the trachea of the animal where it has the greatest likelihood of reaching the lung.

Another advantage of the invention is to provide a system for delivering dry medicaments in gaseous suspension to the lungs of animals during the inhalation phase of the respiration, and thereby achieving uniform distribution of the medicament to the greatest possible surface area of the organ.

Another advantage of the invention is to provide a system for injecting a medicament in a gaseous suspension into the trachea of an animal while simultaneously directing a stream of gas into the mouth and nose of the animal to assist in directing and carrying the medicament into the lungs and in expanding the lungs to achieve maximum distribution of the medicament to affected areas.

The system of the present invention also provides a means for delivering a large dosage of a dry medicament to the lungs of an animal in a short period of time. The invention is further intended to provide a portable inhalation therapy system which can be carried by a veterinarian into the field to treat animals having respiratory diseases. A still further advantage of the invention is to provide an inhalation therapy system for livestock which can be operated with a minimum amount of distress to the animal.

SUMMARY OF THE INVENTION

The present invention provides a system for the injection of medicaments into the trachea of an animal. The system comprises: needle means for insertion into the trachea of the animal, said needle means having a passageway for directing the medicament into the trachea in the direction of the lung; medicament dispensing means for dispensing the medicament into said needle means; mask formed of a substantially gas impermeable material and shaped to fit over the animal's nose and mouth and having an opening for the movement of gas thereto; and regulator means connected to said needle means and to said mask opening. The regulator means which is adapted for connection to a supply of compressed gas, directs and times the flow of the gas under pressure to the needle means and to the opening of the mask to coincide with the animal's inhalation. The regulator means comprises: a breathing tube attached to the opening of the mask; means in said tube for permitting the escape of air above a predetermined pressure from said tube; an intermittant positive pressure breathing unit (IPPB unit) attached to said breathing tube and attached to the needle means for controlling the release of gas into said breathing tube and into said needle means; and means connected to said IPPB unit for responding to changes in pressure in the tube caused by the animal's respiration. Negative pressure changes in the tube are sensed by the IPPB unit and trigger the unit to discharge pressurized streams of gas into the breathing tube and to the medicament dispenser. Gas released by the IPPB unit will expand the lungs to insure maximum distribution of the medicament throughout the organ. The negative pressure in the mask and breathing tube which triggers the IPPB unit is created by the animal's inhalation. The medicament is picked up by the gas stream and carried via the needle means into the trachea. At the same time, gas is being supplied via the mask to the nose and mouth of the animal and into the trachea, thereby assisting in propelling the medicament into the lungs. When sufficient pressure has been built up in the animal's lungs, the IPPB unit shuts off the streams of compressed gas and the animal is allowed to exhale normally through the exhalation valve in the breathing tube. When the animal takes his next breath, the IPPB unit is again triggered and the cycle is repeated. The system is operated until the animal receives the entire dosage of medicament.

DESCRIPTION OF THE DRAWINGS

Understanding of the invention will be facilitated by reference to the accompanying drawings in which like numbers refer to like parts in several views and wherein:

In FIG. 1 a system is illustrated for injecting a medicament into the trachea 10 of an animal 12 comprising needle means 14 for insertion into trachea 10 connected to the top of medicament dispenser 16. The lower portion of the medicament dispenser 16 is connected by tube 18 to the IPPB unit 20. The IPPB unit 20 is fitted with three other connections. Tube 22 connects the IPPB unit 20 with regulator 24 which regulates the pressure of the gas released from a source of compressed air such as an air or oxygen cylinder 26. Breathing tube 28 connects the IPPB unit to the mask 30 which fits over the nose and mouth of animal 12 in a substantially air-tight fashion. Breathing tube 28 contains an exhalation valve assembly 32 which allows air above a predetermined pressure to escape and which responds to pressure changes in breathing tube 28. Responses by valve assembly 32 to changes in pressure in the breathing tube 28 are sensed by the IPPB unit 20 by way of tube 34.

FIG. 2 illustrates the presently preferred embodiment of mask 30. When fitted over the animal's nose and mouth, the mask must be air tight to the extent that it can maintain positive and negative pressures created by the animal's respiration long enough for these pressure changes to be detected by the IPPB unit. The materials used to form the mask must, therefore, be substantially gas impermeable. In FIG. 2, mask 30 is comprised of a nose cap 36 formed from a high impact moldable plastic such as a polyolefin or ABS (acrylonitrile-butadiene-styrene). The function of the rigid nose cap is to prevent the end of the mask from collapsing around the animal's nostrils and thereby preventing the flow of air to the animal.

Figure 1:
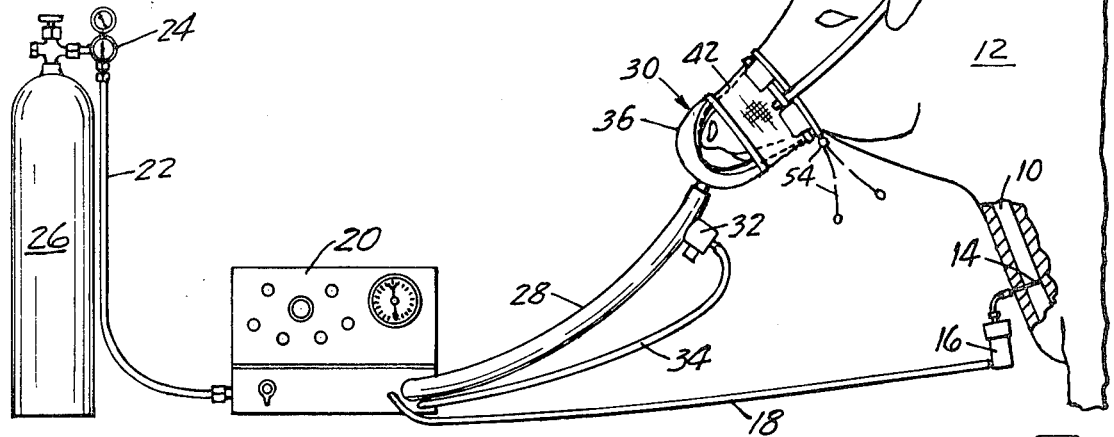
FIG. 1 is a schematic diagram of the entire tracheal injection system of the present invention.

Nose cap 36 contains an opening 38 which is fitted with an attachment for the breathing tube 28. Fitted snuggly within the nose cap 36 is a nose frame 40 comprising a generally circular band 42 and a pair of arcuate bands 44 secured thereto. Nose frame 40 functions as a rigid, gas permeable abutment for the animal's nose to prevent the nose cap 36 from resting tightly against the animal's nose, in which position the flow of air to the animal's air passages might be prevented. Nose frame 40 insures therefore, that ample clearance is provided for the free flow of air to the animal's nose. Nose frame 40 also allows the same mask to be fitted onto animals of varying sizes by eliminating the risk that the nose of a smaller animal will become lodged tightly against the front of the mask. Nose frame 40 can be formed from any rigid, light-weight material such as molded plastic or aluminum strappings and the design can vary widely so long as large air openings are provided in its structure.

The bag or snout section 46 is attached with an airtight seal to nose cap 36. Snout section 46 is made from a gas impermeable material which is flexible enough to allow for adjustment when fitting a variety of snout sizes. It has been found that rubberized or coated nylon tent fabric works well for this purpose as well as polyethylene. Snout section 46 can be sealed to nose cap 36 with a tent fabric seam sealer adhesive (available from Eureka Tent and Awning, Binghamton, N.Y.).

Figure 2:
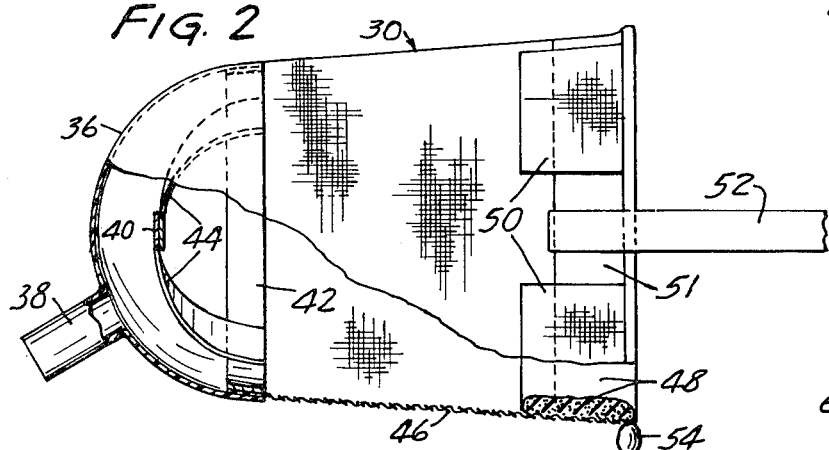
FIG. 2 is a side view of a mask partially in section.

The open end of snout section 46 is fitted on the interior surface with a gasket 48 of closed cell foam which aids in forming a substantially air tight seal when the mask is tightened around the animal's snout. The mask may be tightened around the animal's snout in a variety of ways. For example, draw string means may be provided about the open end of the snout section 46. FIG. 2 illustrates broad belt loops 50 which are heat sealed to the exterior open end of snout section 46. A belt 51 is fitted through belt loops 50 and tightened by conventional belt or strap fastening means.

The mask may have optionally a head strap 52 which fits over the back of the head of the animal to hold the mask in place over the snout. Another optional feature is an immobilizing cinch 54. Cinch 54, if present, should be made of sturdy material such as wire rope or nylon strap. The cinch is equipped with a rope lock to hold it tightly until released. The cinch functions to restrain the animal's head from movement while the trachea is punctured and the system is operated. The cinch may be held tightly by an assistant or if a structure such as a stanchion is present, the cinch can be anchored to the structure.

Figure 3:
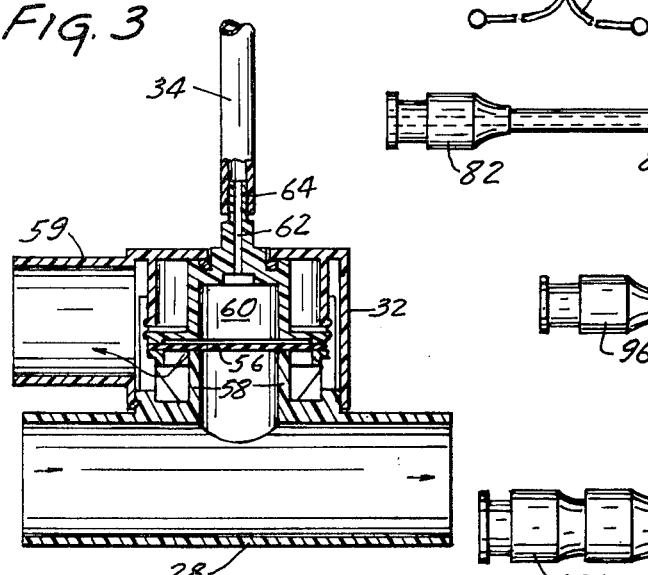
FIG. 3 is a vertical sectional view of the exhalation valve assembly which contains means for detecting and transmitting pressure changes in a breathing tube.

In FIG. 3 the exhalation valve assembly 32 in the breathing tube 28 is shown in detail. This valve assembly functions to allow air above a predetermined pressure to escape from the mask and breathing tube and also to provide a means which responds to pressure changes in the mask and breathing tube which responses are detected by the IPPB unit. Exhalation valve assembly 32 is commercially available from Minnesota Mining and Manufacturing Company, St. Paul, Minn., U.S.A. as the exhalation valve from the MA-1 Manifold Nebulizer 3082. This commercial item is equipped with a nebulizer chamber which is unnecessary in the present system and can be removed. Another suitable exhalation valve assembly termed an "intermittent positive pressure breathing manifold" is described in U.S. Pat. No. 3,826,255 issued to Haystad et al. on July 30, 1974.

The essential feature of the exhalation valve assembly is a flexible, gas impermeable, essentially flat membrane or diaphragm 56 which is releasably positioned over the opening of the lateral tube 58 which communicates with breathing tube 28. When the animal exhales diaphragm 56 is forced upward and air is allowed to escape to the outside around the diaphragm 56 above tube 58 and out through release tube 59. An air chamber 60 is present on the opposite side of the diaphragm 56 from tube 58. Chamber 60 is closed to external air at all times and diaphragm 56 forms one wall thereof. Chamber 60 has an opening 62 to which is fitted with attaching sleeve 64 which connects to the tube 34 and the IPPB unit 20. As the animal inhales, the diaphragm is pulled downward by negative pressure in the breathing tube and seals the tube 58 from the external air. At the same time, a negative pressure is thereby created in chamber 60 and sleeve 64 which pressure change is detected by the IPPB unit 20. The IPPB unit 20 is thereby triggered to discharge compressed air.

Figure 4:
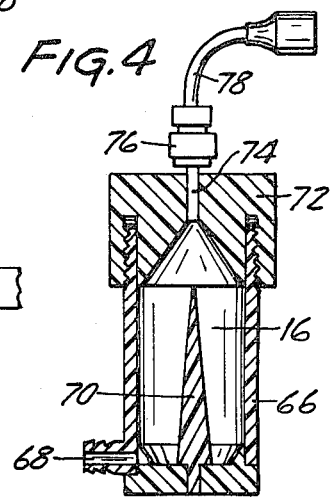
FIG. 4 is a vertical sectional view of the medicament dispenser.

FIG. 4 illustrates the presently preferred embodiment of the medicament dispensing means 16 which comprises a circular cup-shaped member 66 which has a smooth interior surface substantially free from crevices or corners to retain portions of the medicament. A side opening 68 is present at the base of cup 66 which opening is connected to the high pressure gas line 18 attached to the IPPB unit 20. Cup 66 contains a conical center post 70 which functions to enhance the pick up of the medicament by the whirlwind action of the air stream entering from opening 68. A vortex effect is observed as pressurized air enters opening 68 and the medicament is carried upward in a swirling manner. Conical center post 70 prevents the medicament from settling in the dead space created in the center of the vortex.

Cap 72 is fitted with screw-on means to facilitate easy removal for loading of the medicament. The interior surface of cap 72 is tapered inward in a conical fashion to form a reduced opening 74 at the apex, from which opening the gas-suspended medicament emerges. This tapered interior insures that substantially all of the medicament is discharged from the cup 66. The exterior portion of the cap 72 is fitted with an adaptor 76 for connecting the opening 74 to the needle means 14 by needle adaptor means 78.

Figure 5:
FIGS. 5, 6, 7 are elevational views, partially in vertical section, of alternative embodiments of the needle means.
Figure 6:
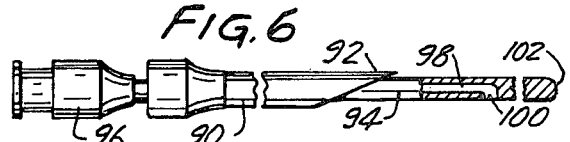

FIG. 5 illustrates one embodiment of the needle means 14 which comprises a needle 80 having an adaptor 82 which connects with needle adaptor means 78 of the dispensing means 16. Needle 80 contains passageway 84 for carrying the medicament into the trachea and a discharge side port 86. Needle 80 has a closed pointed tip 88 for penetrating the neck tissue and the trachea. The interior wall of the closed tip of the needle serves an impact surface to break up any agglomerated medicament inpinging thereon. It is preferred that the tip 88 be closed in order to prevent coring during penetration of the animal and the side port 86 assures proper directional discharge of the medicament. The size of the needle may preferably range from 13 to 16 gauge, with a 15 gauge needle being the most preferred. The length of the needle can vary greatly but the side port 86 should be located in relation to pointed tip 88 such that the medicament can be released in substantially the central portion of the trachea.

FIG. 6 illustrates the presently preferred embodiment of the needle means 14. In this embodiment, a needle catheter 90 having a beveled tip 92 is first inserted into the trachea. The needle catheter is preferably fitted with a removable plug to prevent coring during the puncture of the trachea. When the needle catheter 90 is in place in the trachea, the plug is removed and needle 94 is inserted through the catheter needle 90. Needle 94 is connected via adaptor 96 to needle adaptor means 78 of the dispensing means 16. Needle 94 contains a passageway 98 for carrying the medicament into the trachea. Passageway 98 terminates in side port 100, located at the proper distance from closed rounded tip 102 such that when tip 102 abuts against the interior far wall of the trachea, the side port 100 is positioned substantially in the center of the trachea. The end wall of passageway 98 provides an impact surface for breaking up any agglomerated medicament before discharge into the air stream of the trachea. The catheter needle 90 is preferably a 12 gauge needle and the needle inserted therethrough is preferably a 15 gauge needle.

FIG. 7 illustrates a further embodiment of the needle means 14 for practicing the present invention. A catheter needle 101 is used in this embodiment. A needle 104 is equipped with an adaptor 106 to connect with needle adaptor means 78 of the dispensing means 16. Needle 104 can preferably be an extruded construction comprising parallel passageways 108 and 110 terminating at an end formed with a tip and a mixing chamber 112 for mixing streams of medicament from passageways 108 and 110 and directing the medicament into the trachea through a side port 114. Side port 114 is located at a proper distance from the rounded closed tip 116 to insure that when tip 116 abuts against the interior far wall of the trachea, the side port 114 is positioned substantially in the center of the trachea. The tip can be formed by a cap secured to the extruded needle structure or by filling, i.e. brazing. The needle may be plastic or aluminum. The opening through the catheter needle may be oblong and the cross-section of this needle may be oblong to accommodate the parallel passageways 108 and 110.

Figure 8:
FIG. 8 is a cross-sectional view taken along line 8—8 of FIG. 7.
Figure 7:
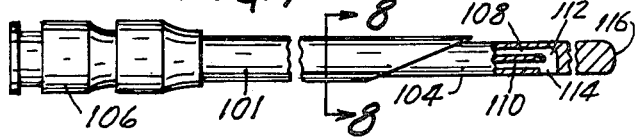

FIG. 8 illustrates a cross-sectional view of oblong catheter needle 101 having inserted therein oblong needle 104 having parallel passageways 108 and 110. It is possible to provide separate adaptors for each passageway so that one passageway may be connected to the high pressure tube 18 and carry only pressurized gas while the other passageway carries the gas suspended medicament. The pressurized gas from one passageway will mix with the gas-suspended medicament carried by the other passageway in the mixing chamber and thereby aid in breaking up any agglomerated medicament.

The IPPB unit utilized in the system of the present invention is commercially available. The presently preferred model is a Monaghan "M520 I.P.P.B." This unit is available from Monaghan, 4100 East Dry Creek Road, Littleton, Colo. 80122, U.S.A.

The IPPB unit can be connected to any source of compressed gas such as a gas cylinder, a piping system or an air compressor. Generally compressed air will be used to carry the medicament into the trachea of the animal, but compressed gas having varying oxygen contents may also be used.

The pressure of the gas which is discharged by the IPPB into the medicament dispenser is significantly higher than the pressure of the gas which is discharged by the IPPB unit into the mask. The pressure of the gas discharged to the mask will be that pressure required to inflate the lungs of the particular animal being treated. It will, therefore, vary with the size and position of the animal under treatment but will generally be about 18 to 20 cm. of water. When treating adult cattle it has been found that a pressure of 20 cm. of water is preferred for adequate inflation of the lungs when the animal is in a standing position.

The higher pressure of the gas used to suspend the medicament and force it into the trachea can vary from 15 psi (1.05 kg/cm$^2$) to 30 psi (2.10 kg/cm$^2$) but is preferably about 20 psi (1.41 kg/cm$^2$).

It has been found that the Monaghan "M520 I.P.P.B." unit delivers approximately 20 to 25 cubic ft/hr (550 to 700 liters/hr) of gas to the medicament dispenser.

Any medicament in dry, particulate form may be delivered to the lungs of the animal using the system of the present invention. For best results, however, it is preferred to use a dry medicament powder containing particles in the size of 1 to 6 microns. A particle size of about 3 microns is preferred in order for the particles to reach the smallest recesses of the lungs where the medicament can assert its greatest therapeutic effect. The medicament should be as free-flowing as possible in order to provide a uniform gas-suspension and in order to minimize the formation of agglomerates.

When operating the system of the present invention, the medicament dispenser is first loaded with the desired dosage of medicament. The mask is then placed over the animal's nose and mouth and tightly secured. It is next desirable to make the tracheal puncture with the catheter needle. To prevent coring out a section of the animal during puncture and to prevent the catheter needle from clogging, it is desirable to place a removable plug inside the catheter needle which is later removed after the catheter needle is in place in the trachea. It is preferable to make the puncture as far down on the trachea as possible in order to minimize the distance which the gas-suspended medicament must travel before reaching the lungs. The puncture should be made between consecutive cartilage rings of the trachea for easy penetration.

Once the catheter needle is in place in the trachea and the plug removed, the mask can be attached to the breathing tube and the needle extension of the medicament dispenser can be inserted into the catheter needle. When all the elements of the system are connected the IPPB unit is turned on and compressed gas is supplied to the mask and the medicament dispenser, intermittantly, in response to the animal's breathing.

The treatment period will vary somewhat depending upon the dosage of drug being administered. It has been found that when treating an adult cow, thirty seconds of operation is sufficient to insure complete delivery of a 500 milligram dosage of medicament containing essentially spherical particles of less than 6 microns in diameter.

It is possible, therefore, to efficiently deliver a large dosage of dry medicament to the lungs of an animal in a very short period of time using the system of the present invention. Because of the shortness of the treatment period required, the animal is subjected to a minimum amount of discomfort. The system of the present invention is especially suited for treating livestock such as cattle, horses and swine, but by modifying the size of the respiratory mask and needles used, the system is adaptable to a wide variety of animal species.

What is claimed is:

1. In combination:
    a catheter needle comprising a hollow tube with a beveled end for penetrating the skin of an animal to project the beveled end into the trachea; and
    a needle fitting through said catheter needle comprising an elongated rod-like member terminating at one end in a blunt tip, said needle having a first closed passageway extending lengthwise through said rod-like member for transmitting gas-propelled dry medicament and terminating at an end wall spaced a sufficient distance from said blunt tip to insure that said end wall is positioned near the center of the trachea when the blunt tip engages the wall of the trachea, said end wall defining an impinging surface for breaking up agglomerates of dry medicament, and a second closed passageway parallel to said first closed passageway, said parallel passageways communicating with each other immediately adjacent to said end wall so that materials passing through said passageways are mixed, and said rod-like member having a single side port communicating directly with said passageways and said end wall for directionally discharging dry medicament propelled through said passageways into the trachea.

* * * * *